(12) United States Patent
Wu et al.

(10) Patent No.: US 9,708,640 B2
(45) Date of Patent: Jul. 18, 2017

(54) ELECTROSPUN NANOFIBROUS MEMBRANES AND DISPOSABLE GLUCOSE BIOSENSOR

(71) Applicant: National Taiwan University of Science and Technology, Taipei (TW)

(72) Inventors: Chang-Mou Wu, Taipei (TW); Hsiu-An Yu, Taipei (TW); Chun-Chung Huang, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 29 days.

(21) Appl. No.: 14/791,872

(22) Filed: Jul. 6, 2015

(65) Prior Publication Data
US 2016/0153025 A1 Jun. 2, 2016

(30) Foreign Application Priority Data

Dec. 1, 2014 (TW) .............. 103141679 A

(51) Int. Cl.
| | |
|---|---|
| C12Q 1/54 | (2006.01) |
| C12N 9/04 | (2006.01) |
| C12Q 1/00 | (2006.01) |
| G01N 27/327 | (2006.01) |
| B82Y 15/00 | (2011.01) |

(52) U.S. Cl.
CPC .............. *C12Q 1/54* (2013.01); *C12N 9/0006* (2013.01); *C12Q 1/004* (2013.01); *C12Q 1/006* (2013.01); *G01N 27/3272* (2013.01); *G01N 27/3278* (2013.01); *B82Y 15/00* (2013.01); *C12Y 101/03004* (2013.01)

(58) Field of Classification Search
None
See application file for complete search history.

(56) References Cited

U.S. PATENT DOCUMENTS

2007/0287191 A1* 12/2007 Stiene ................. A61B 5/1486
436/150

OTHER PUBLICATIONS

Su et al.,"A novel platform for enhanced biosensing based on the synergy effects of electrospun polymer nanofibers and graphene oxides", Analyst 138: 1459-1466 Dec. 2012.*
C.M. Wu et al., IUPAC World Polymer Congress—Macro 2014, publication, Jul. 6-11, 2014, Taiwan.

* cited by examiner

*Primary Examiner* — Anand Desai
(74) *Attorney, Agent, or Firm* — Alan D. Kamrath; Kamrath IP Lawfirm, P.A.

(57) ABSTRACT

An electrospun nanofibrous membrane is sheet like and is formed by multiple glucose oxidase/potassium hexacyanoferrate(III) modified electrospun nanofibers. The glucose oxidase/potassium hexacyanoferrate(III) modified electrospun nanofibers are PVA electrospun nanofibers containing glucose oxidase and potassium hexacyanoferrate(III) homogeneously dispersed therein. The glucose oxidase/potassium hexacyanoferrate(III) modified electrospun nanofibers are PVA electrospun nanofibers and are cross-linked by glutaraldehyde vapor with ultrasonic energy assistance. Graphene modified PVA/GOx electrospun membranes were prepared to examine the immobilization mechanism between graphene and GOx. The electrochemical measurement results show that the sensitivities increased with increasing graphene concentrations up to 20 ppm. The highest sensitivity recorded 38.7 μA/mM was for a PVA/GOx membrane with 20 ppm graphene representing a 109% increase over a membrane made without graphene.

6 Claims, 16 Drawing Sheets

ELECTROSPUN NANOFIBROUS MEMBRANES AND DISPOSABLE GLUCOSE BIOSENSOR

BACKGROUND OF THE INVENTION

1. Field of Invention

This invention relates to nanofibrous membranes and, more specifically, to nanofibrous membranes for a disposable biosensor.

2. Description of the Related Art

Diabetes is an increasingly important worldwide public health problem. The metabolic disorder results from either insulin deficiency, in type 1 diabetic patients, or from insulin resistance and its complications in type 2 patients. Both conditions can result in hyperglycemia leading to blood glucose concentrations higher than the normal range 80-120 mg/dL (4.4-6.6 mM). The diagnosis and management of diabetes require the careful monitoring of blood glucose levels. The glucose bio-sensor has thus become one of the most important physiological monitoring devices, accounting for about 85% of the entire biosensor market.

A biosensor is a device which combines an immobilized bio-recognition element with a transducer. It can monitor chemical substances on the inside or outside of an organism by generating a signal representative of the analyte's concentration after coupling the biochemical and transducer reactions. Glucose biosensors are based on electrochemical principles and frequently employ enzymes as the biological recognition element. The biosensor's performance and sensitivity often strongly depend on the influence imposed on the enzyme's structure by immobilization. Such influences result from the choice of the host molecule and the immobilization method used.

In attempts to retain enzymatic activity and stability various molecules have been used to immobilize enzymes on different substrates, e.g. poly(vinyl alcohol) (PVA), poly (ethylene oxide) (PEO), chitosan, polymethylmethacrylate (PMMA), poly(vinyl pyrrolidone) (PVP) and polyurethane (PU). PVA is often used as an immobilization matrix because of its inherent nontoxicity, high thermal stability, good biocompatibility and its desirable physical properties such as its elastic nature, good film forming properties, and its high degree of swelling in aqueous solutions—all of which contribute to making it a good matrix for enzyme immobilization. Different methods, such as the cross-linking of PVA, freeze-thawed PVA, and enzyme encapsulation in PVA/silicate hybrid materials, have been successfully employed to immobilize the enzyme molecules in various membranes. However, due to the compaction and low-conductivity of the PVA membrane, substrate infiltration and electron transfer between the enzyme membrane and the electrode remain problematic.

SUMMARY OF THE INVENTION

In order to solve the disadvantages and shortcomings of the conventional glucose biosensors, the present invention provides electrospun nanofibrous membranes and a glucose biosensor to obviate or mitigate the shortcoming of the prior art.

An electrospun nanofibrous membrane is formed by multiple electrospun nanofibers. The electrospun nanofibers are electrospun by a matrix material solution and contain glucose oxidase and potassium hexacyanoferrate(III) homogeneously dispersed therein, and the electrospun nanofibers are cross-linked by glutaraldehyde vapor or heat treatment.

Thus, the present invention achieves advantages as below.

1. The present invention is able to solve the interference problem from H2O2 during blood testing by using the potassium hexacyanoferrate(III) salt, with the potassium hexacyanoferrate(III) also being low cost.

2. The present invention is able to enhance the sensitivity of the glucose biosensor by adding the conductive material.

3. The present invention may be successfully applied on the disposable glucose biosensor. The glucose biosensor has many advantages like being easy to use, of low cost and having fast reaction time.

DETAILED DESCRIPTION OF THE INVENTION

Figure 1:
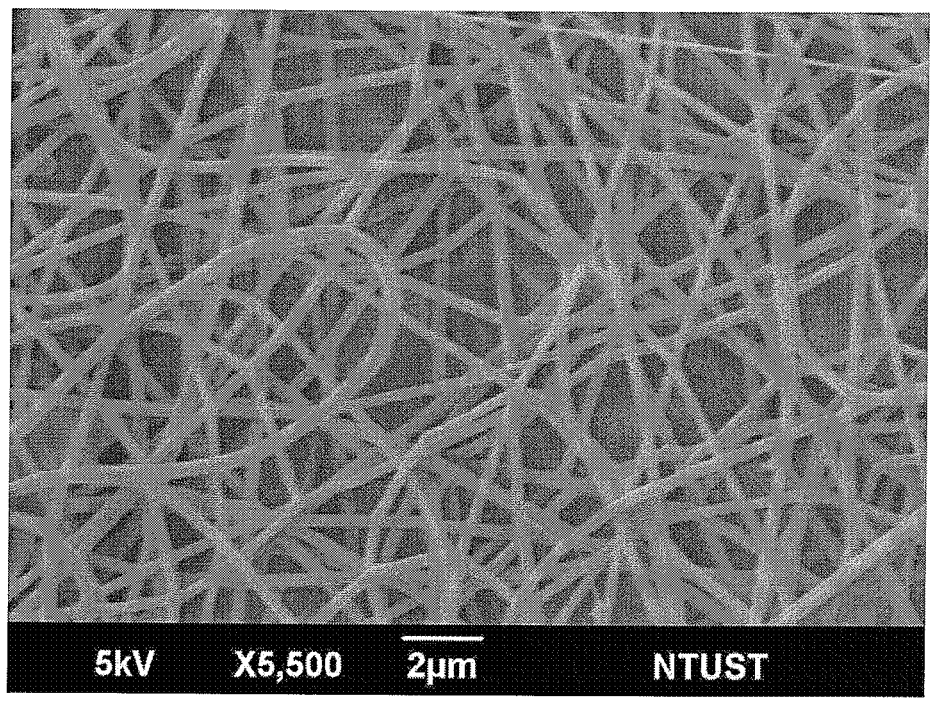
FIG. 1 is a SEM observation result of a electrospun nanofibrous membrane in accordance with the present invention.

A producing method of an electrospun nanofibrous membrane has steps comprising providing a matrix material solution, and the matrix material solution may be a polyvinyl alcohol (PVA) solution, a poly(ethylene oxide) (PEO) solution, a chitosan solution, a polymethylmethacrylate (PMMA) solution, a poly(vinyl pyrrolidone) (PVP) solution or a polyurethane (PU) solution;

forming an electrospun solution, with the electrospun solution formed by mixing glucose oxidase (GOx) and potassium hexacyanoferrate(III) ($K_3[Fe(CN)_6]$) into the matrix material solution, and the matrix material may be a PVA solution in a preferred embodiment of the present invention; and electrospinning the electrospun solution to form the electrospun nanofibrous membrane. The electrospun nanofibrous membrane is formed as being sheet-like and is collected from multiple electrospun nanofibers. The electrospun nanofiber is formed by a mixture of a matrix material solution, glucose oxidase and potassium hexacyanoferrate(III).

The matrix material solution may further comprises a conductive material. The conductive material may be graphene, nano-gold (Au with nano scale particle sizes), graphene oxide, or carbon nanotube. The conductive material increases conductivity and provides better electrical signal transportation of bio-signals during practical use.

The graphene may be graphene oxide. The graphene is designed to open an outer shell of the glucose oxidase to facilitate electrons transferring into an active redox center of the glucose oxidase. Thus, a sensitivity of the electrospun nanofibrous membrane of the present invention is further enhanced.

Concentration of above mentioned PVA solution may be but is not limited to 5 wt %~10 wt %. The concentration may be adjusted according to the producing environment, equipment being used and the voltage adopted of the electrospun. The molecular weight of the PVA polymer in the PVA solution may be but is not limited to 10000~20000. The solid content of the PVA in the electrospun nanofibrous membrane may be but is not limited to 90%~96%. The solid content of the glucose oxidase in the electrospun nanofibrous membrane may be but is not limited to 1~3%. The solid content of the potassium hexacyanoferrate(III) in the electrospun nanofibrous membrane is about 2~8%. The solid content of the nano-gold in the electrospun nanofibrous membrane is about 10~2000 ppm. The solid content of the graphene in the electrospun nanofibrous membrane is about 10~2000 ppm.

The present invention may further comprise a cross-linking step after electrospinning. The cross-linking step may use glutaraldehyde vapor or heat treatment to enhance or increase the electrospun nanofibers being cross-linked. The cross-linking step may also be enhanced with using an ultrasonic source. Cross-linked nanofibers of the present invention may have a better enzyme immobilization result after the cross-linking step.

Since electrospun PVA is water-soluble polymer and has a high surface area, a vapor form glutaraldehyde is preferred to be used to avoid the PVA nanofibers being dissolved in a liquid form glutaraldehyde solution. The ultrasonic source is used to speed up the cross-linking process of the PVA nanofibers to prevent the aforementioned dissolved issue.

The heat treatment cross-linking method is heating up the electrospun nanofibrous membrane at a temperature around 50° C.~145° C.

In practical use, the electrospun nanofibrous membrane of the present invention may be produced as a disposable glucose biosensor. The electrospun nanofibrous membrane is attached on a disposable assembly. The disposable assembly comprises a sensor body and an electrode set. The electrode set is mounted on or printed on the sensor body.

The electrode set of the disposable assembly may be a screen-printed carbon electrode. PVA, the glucose oxidase and the potassium hexacyanoferrate(III) are uniformly dispersed.

The general redox reaction equations of the conventional glucose biosensor are as follows.

$$\beta\text{-Glucose} + GOx_{(ox)} \rightarrow \text{Gluconic acid} + GOx_{(red)}$$
$$GOx_{(red)} + O_2 \rightarrow GOx_{(ox)} + H_2O_2$$

$$H_2O_2 \rightarrow O_2 + 2H^+ + 2e^-$$

The reaction equation may change after adding the potassium hexacyanoferrate(III) in the present invention. The alter redox reaction equations are as follows.

$$\beta\text{-Glucose} + GOX_{(ox)} \rightarrow \text{Gluconic acid} + GOX_{(red)}$$

$$GOX_{(red)} + Fe^{3+} \rightarrow GOX_{(ox)} + Fe^{2+}$$

$$Fe^{2+} \rightarrow Fe^{3+} + e^-$$

With reference to above equations, the required voltage of the whole reaction may be reduced by the potassium hexacyanoferrate(III). The interference of the whole reaction may be further reduced by the existence of the potassium hexacyanoferrate(III). The potassium hexacyanoferrate(III) solution is a electrolyte which may be able to dissolve conductive ions to increase the conductivity of the present invention. Thus, the potassium bexacyanoferrate(III) may enhance the electrochemical signal of the present invention.

The conventional glucose biosensor may produce $H_2O_2$ according to above reaction equations. $H_2O_2$ may react with an interference substance in test blood and cause a disturbance reading of the test result. The present invention is able to avoid the interference substance reaction with the $H_2O_2$ in test blood, since the present invention does not produce $H_2O_2$ at room temperature. The interference substance may be urea, uric acid, ascorbic acid (AA) or acetaminophen (AC). The present invention has great sensitivity and selectivity of glucose in test blood which can achieve the excellent test result compared to the conventional glucose biosensors.

Preferred embodiments of electrospun solution in the present invention are as follows.

Embodiment 1

The producing method of a PVA/GOx/potassium hexacyanoferrate(III) electrospun solution having the steps of forming a 7 wt % PVA solution by mixing 7 g PVA and 93 g DI water; and uniformly dispersing 14 mg GOx and 0.46 g of 0.25M potassium hexacyanoferrate(III) solution into 10 g of 7 wt % PVA solution to form the PVA/GOx/potassium hexacyanoferrate(III) electrospun solution.

Embodiment 2

The producing method of a PVA/GOx/potassium hexacyanoferrate(III)/nano-gold electrospun solution having the steps of:

forming a 7 wt % PVA solution by mixing 7 g PVA and 93 g DI water; and uniformly dispersing 14 mg GOx, 0.46 g of 0.25M potassium hexacyanoferrate(III) solution and 0.52 g of 1000 ppm nano-gold solution into 10 g of 7 wt % PVA solution to form the PVA/GOx/potassium hexacyanoferrate(III)/nano-gold electrospun solution.

Embodiment 3

The producing method of a PVA/GOx/potassium hexacyanoferrate(III)/graphene oxide electrospun solution having the steps of:
forming a 7 wt % PVA solution by mixing 7 g PVA and 93 g DI water; and
uniformly dispersing 14 mg GOx, 0.46 g of 0.25M potassium hexacyanoferrate(III) solution and 0.5% graphene oxide solution into 10 g of 7 wt % PVA solution to form the PVA/GOx/potassium hexacyanoferrate(III)/nano-gold electrospun solution.

The parameters of electrospinning are varied to reach suitable properties of electrospun nanofibrous membranes. The preferred embodiment of electrospinning parameters in the present invention may be applying 10 kV~40 kV voltage, 0.1~0.6 (ml/hr) flow rate, 10 cm~25 cm distance from a catching screen to an extruded opening, 1~2 hrs electrospining time or 40+/−5% relative humidity. The electrospun nanofibrous membrane is spun on a PET film.

Preferred embodiments of the disposable glucose biosensor in the present invention are as follows.

Embodiment 1

The producing method of the disposable glucose biosensor in the present invention comprising the steps of:
detaching the nanofibrous membrane of the PET film; and
attaching the nanofibrous membrane on the screen-printed carbon electrode to form the disposable glucose biosensor.

Embodiment 2

The producing method of a cross-linked disposable glucose biosensor in the present invention comprising the steps of:
cross-linking the nanofibrous membrane by the ultra sound assistance cross-linked method with glutaraldehyde vapor;
detaching the cross-linked nanofibrous membrane of the PET film; and
attaching the cross-linked nanofibrous membrane on the screen-printed carbon electrode to form the disposable glucose biosensor.

Physical appearance, chemical properties and electrochemical properties of the present invention and the comparison with the conventional non-electrospun PVA film are as follows. The testing devices are an electrochemical analyzer, a scanning electron microscope (SEM) and a transmission electron microscopy (TEM).

Figure 14:
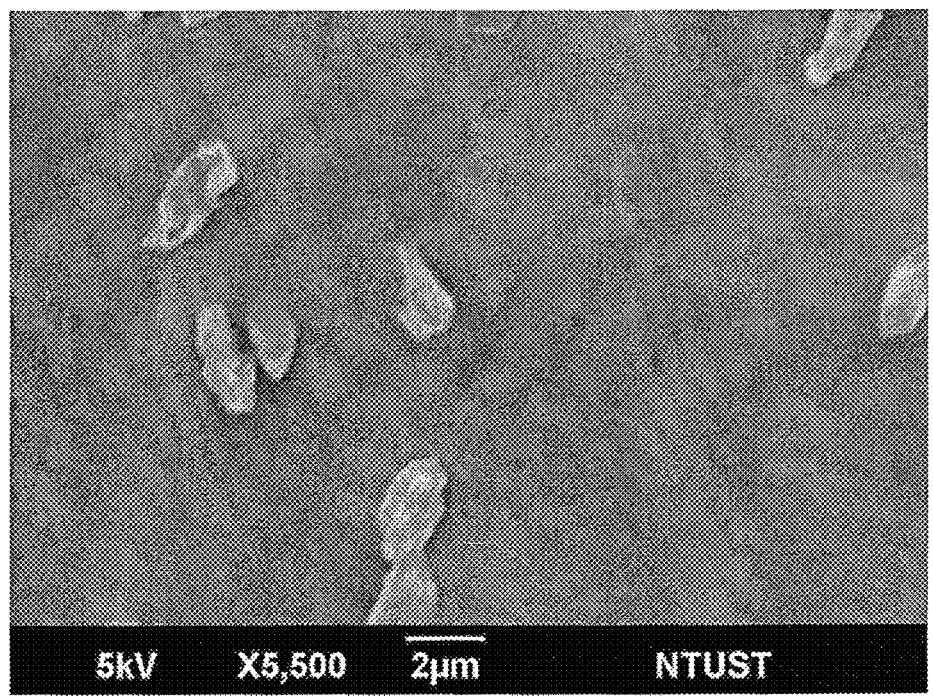
FIG. 14 is a SEM of a conventional non-electrospun PVA film.

With reference to FIG. 1, the SEM pattern shows an average diameter of the present invention is about 296+/−48 nm. With reference to FIG. 14, the SEM pattern shows a surface appearance of the conventional non-electrospun PVA film. The surface appearance of the electrospun nanofibrous membrane is porous-like and has a larger surface area than the conventional non-electrospun PVA film. The electrospun nanofibrous membrane shows a greater surface area than the conventional non-electrospun PVA film. Thus, the present invention may react with more quantity of testing blood and increases the sensibility of the present invention. Surface appearances of the conventional non-electrospun PVA film are almost flat, and crystals are precipitated which may cause bad dispersibility.

Figure 2:
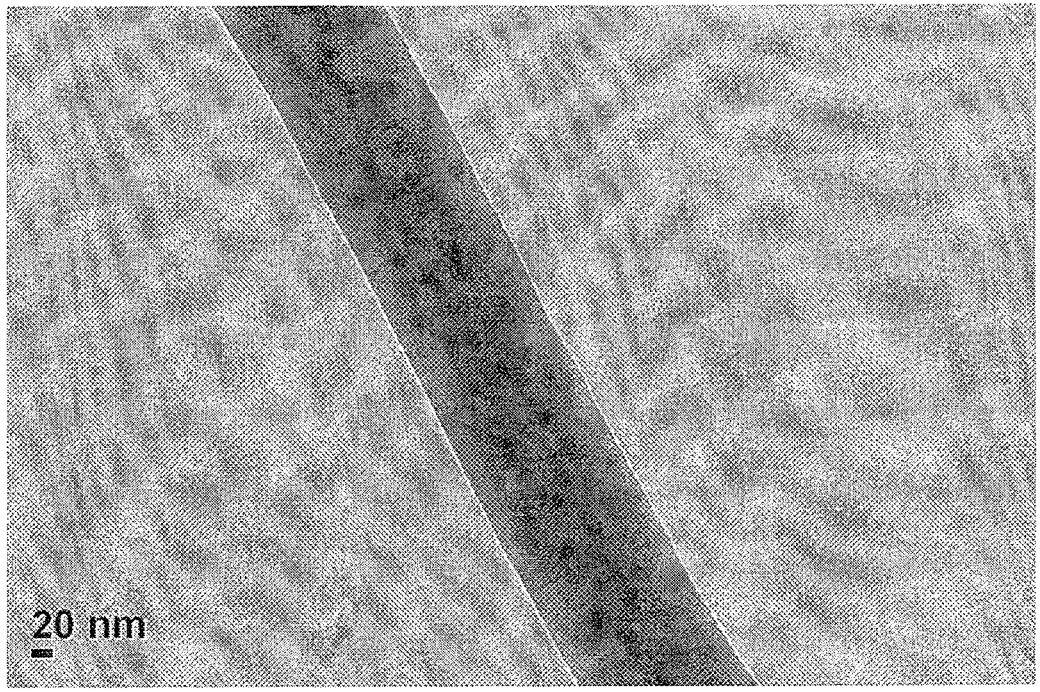
FIG. 2 is a TEM observation result for the electrospun nanofibrous membrane in accordance with the present invention.

With reference to FIG. 2, the TEM pattern shows plenty of black spots in the electrospun nanofiber which indicates that the potassium hexacyanoferrate(III) is successfully dispersed in the electrospun nanofibrous membrane of the present invention.

Figure 3:
FIG. 3 is a TEM of the electrospun nanofibrous membrane in accordance with the present invention.

With reference to FIG. 3, the TEM result shows nano-gold and the potassium hexacyanoferrate(III) are successfully dispersed and attached to the electrospun nanofibrous membrane. The result represents that nano-gold and the potassium hexacyanoferrate(III) may attract to each other causing greater transferring ability for electrons of the present invention.

Figure 4:
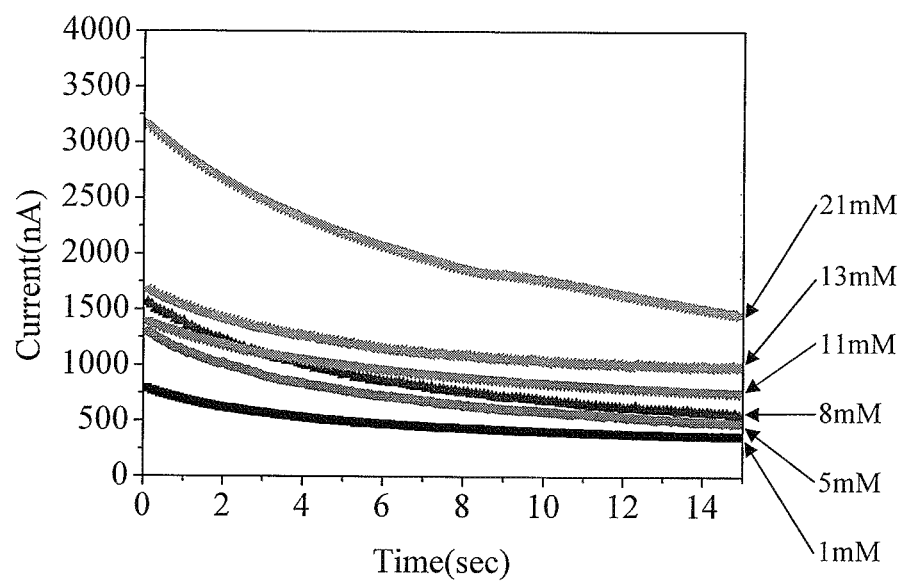
FIG. 4 are current-time curves of different concentration electrospun nanofibrous membrane in accordance with the present invention.
Figure 5:
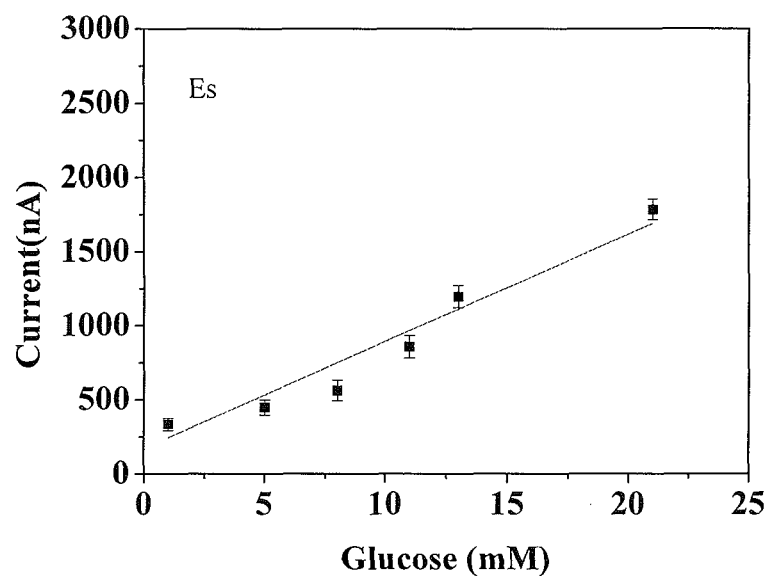
FIG. 5 is a sensitivity testing result of the electrospun nanofibrous membrane in accordance with the present invention.
Figure 6:
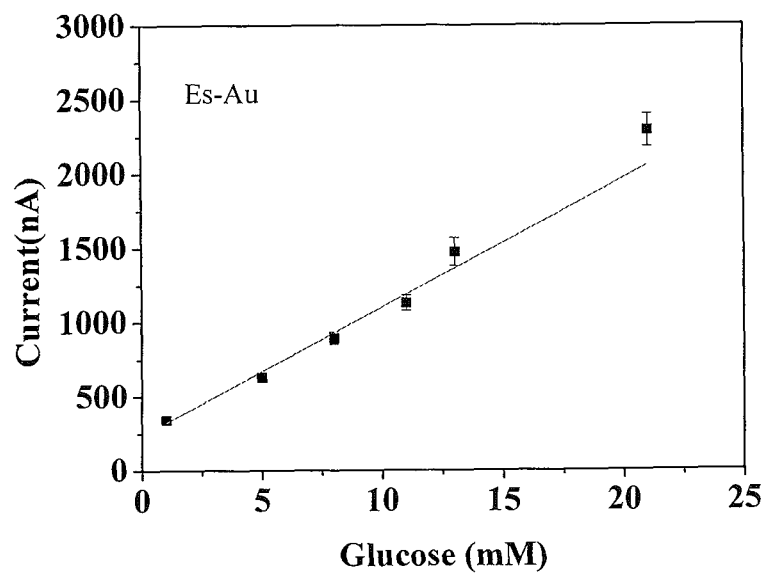
FIG. 6 is a sensitivity testing result of the electrospun nanofibrous membrane in accordance with the present invention.
Figure 7:
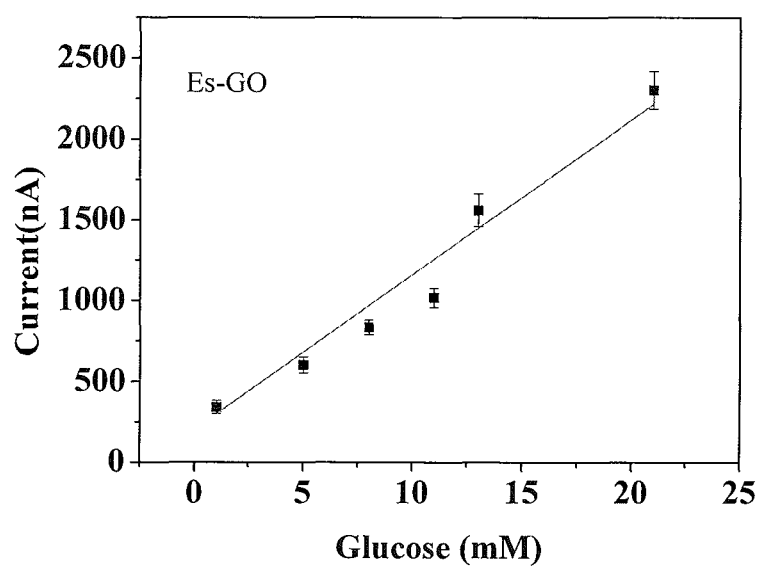
FIG. 7 is a sensitivity testing result of the electrospun nanofibrous membrane in accordance with the present invention.
Figure 8:
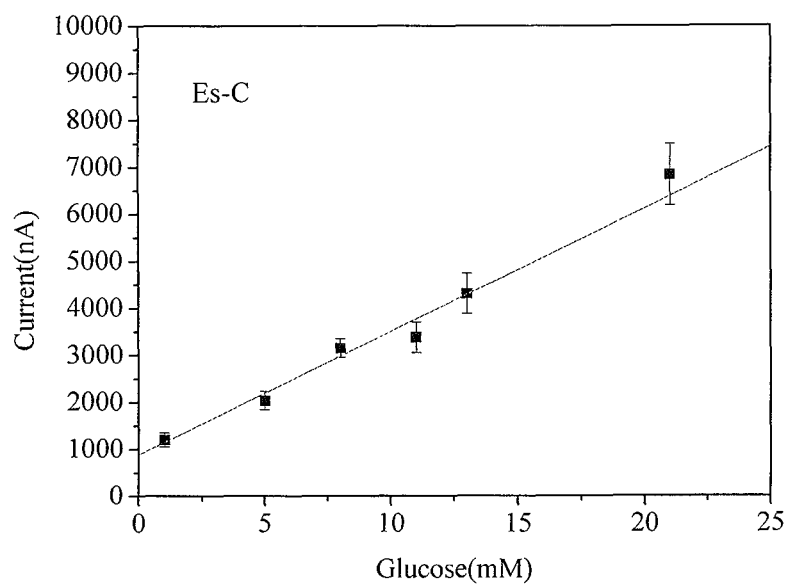
FIG. 8 is a sensitivity testing result of the cross-linked electrospun nanofibrous membrane in accordance with the present invention.
Figure 9:
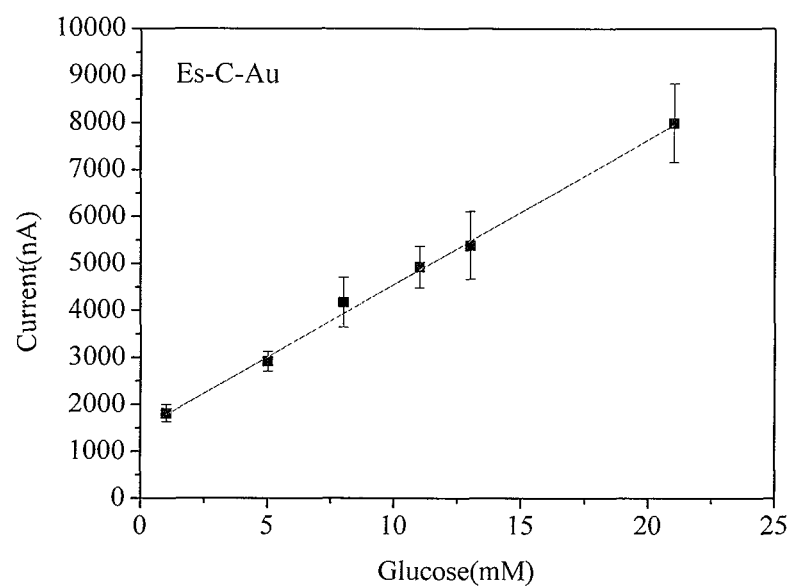
FIG. 9 is a sensitivity testing result of the cross-linked glucose oxidase/potassium hexacyanoferrate(III)/nano-gold modified electrospun nanofibrous membrane in accordance with the present invention.
Figure 10:
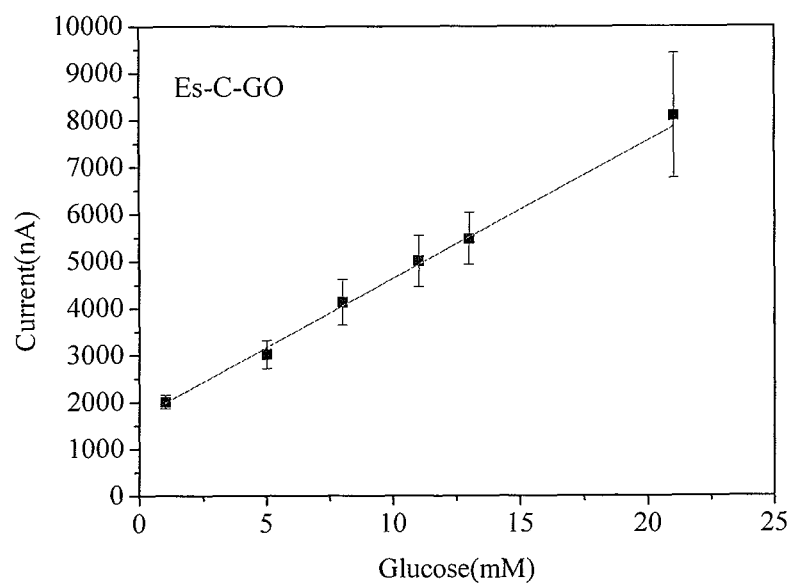
FIG. 10 is a sensitivity testing result of the cross-linked glucose oxidase/potassium hexacyanoferrate(III)/graphene oxide modified electrospun nanofibrous membrane in accordance with the present invention.
Figure 16:
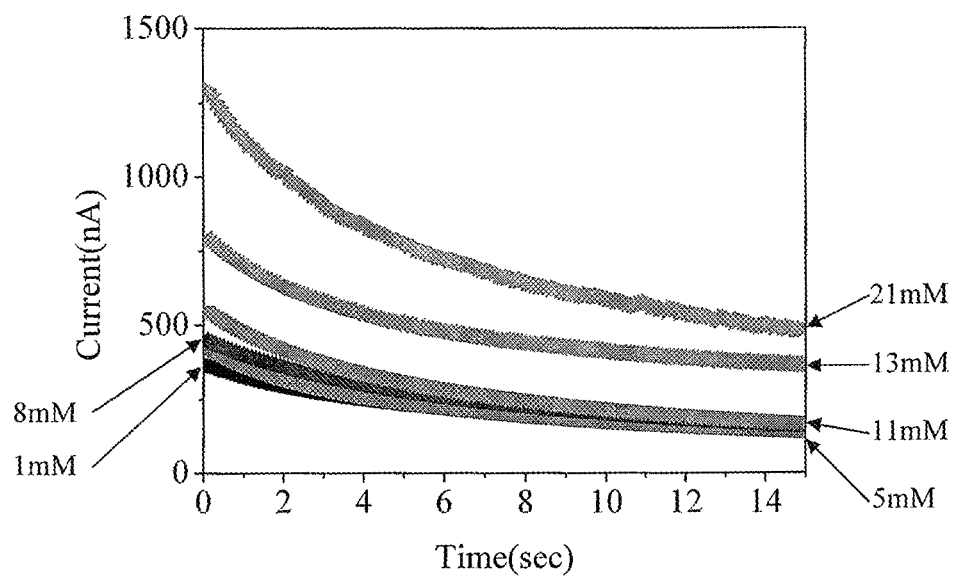
FIG. 16 are current-time curves of the conventional non-electrospun PVA film.

With reference to FIG. 4, the graph of current (nA) against time (sec) of different concentration electrospun nanofibrous membrane shows the highest current value in the present invention is nearly 2000 nA. With reference to FIG. 16, the graph of current (nA) against time (sec) of the conventional non-electrospun PVA film shows the highest current value of the conventional non-electrospun PVA film is only about 1100 nA. The result shows that the glucose oxidase has successfully attached to the present invention which may raise the testing current and enhance the sensitivity of the present invention.

With reference to FIGS. 5~13 and Table 1, a sensitivity testing result of the conventional non-electrospun PVA film and the present invention are shown. The present invention has greater sensitivity than the conventional non-electrospun PVA film. The sensitivity is much greater after the conductive material is further comprised.

TABLE 1

|  | Sensitivity (nA/mM) |
| --- | --- |
| The conventional non-electrospun PVA film(Dip) | 42.69 |
| The electrospun nanofibrous membrane (ES) | 72.26 |
| The glucose oxidase/potassium hexacyanoferrate (III)/nano-gold modified electrospun nanofibrous membrane (ES-Au) | 86.62 |
| The glucose oxidase/potassium hexacyanoferrate (III)/graphene oxide modified electrospun nanofibrous membrane (ES-GO) | 95.81 |

Figure 11:
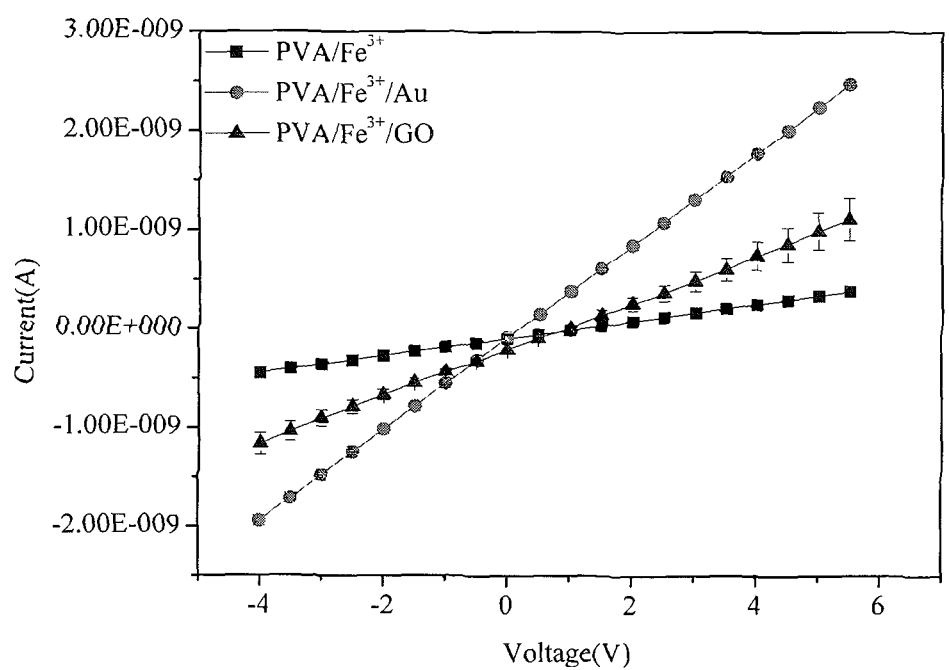
FIG. 11 are current-voltage curves of the glucose oxidase/potassium hexacyanoferrate(III)/conductive material modified electrospun nanofibrous membrane in accordance with the present invention.
Figure 12:
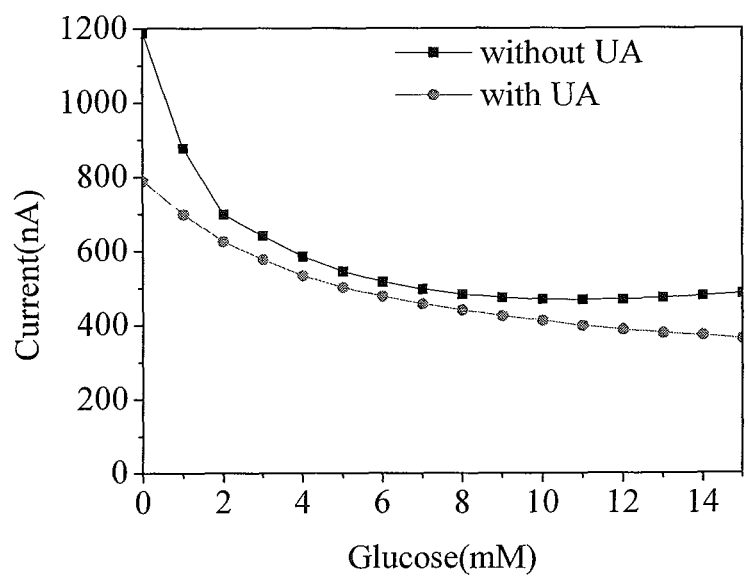
FIG. 12 are current-concentration curves of the electrospun nanofibrous membrane in accordance with the present invention.
Figure 13:
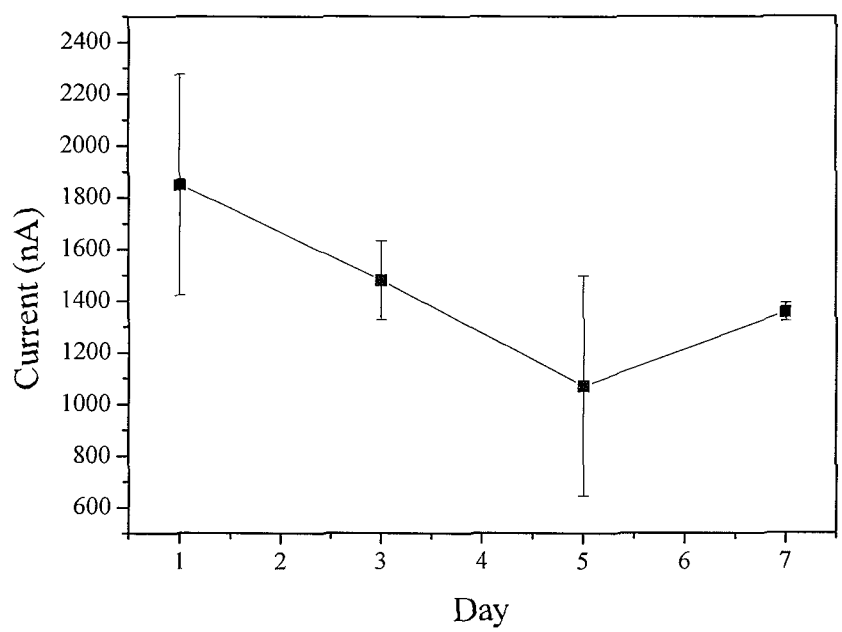
FIG. 13 is a current-time curve of the present invention.

With reference to FIG. 11~FIG. 13 and Table 2, a sensitivity testing result of the present invention after the cross-linked method is shown. The sensitivity of the present invention is enhanced after the cross-linked method.

TABLE 2

|  | Sensitivity (nA/mM) |
| --- | --- |
| The cross-linked electrospun nanofibrous membrane (ES-C) | 262.13 |
| The cross-linked glucose oxidase/potassium hexacyanoferrate (III)/nano-gold modified electrospun nanofibrous membrane (ES-C—Au) | 308.84 |
| The cross-linked glucose oxidase/potassium hexacyanoferrate (III)/graphene oxide modified electrospun nanofibrous membrane (ES-C-GO) | 293.79 |

With reference to FIG. 14 and Table 3, an I-V (resistance) curve of the present invention is shown. I-V curve shows that the resistance value of the present invention is reducing obviously after the conductive material is being further comprised.

TABLE 3

|  | Resistance value (Ω-cm) |
| --- | --- |
| The electrospun nanofibrous membrane (PVA/Fe$^{3+}$) | 7.66E+009 |
| The glucose oxidase/potassium hexacyanoferrate (III)/nano-gold modified electrospun nanofibrous membrane (PVA/Fe$^{3+}$/Au) | 1.43E+009 |
| The glucose oxidase/potassium hexacyanoferrate (III)/graphene oxide modified electrospun nanofibrous membrane (PVA/Fe$^{3+}$/GO) | 2.89E+009 |

Figure 15:
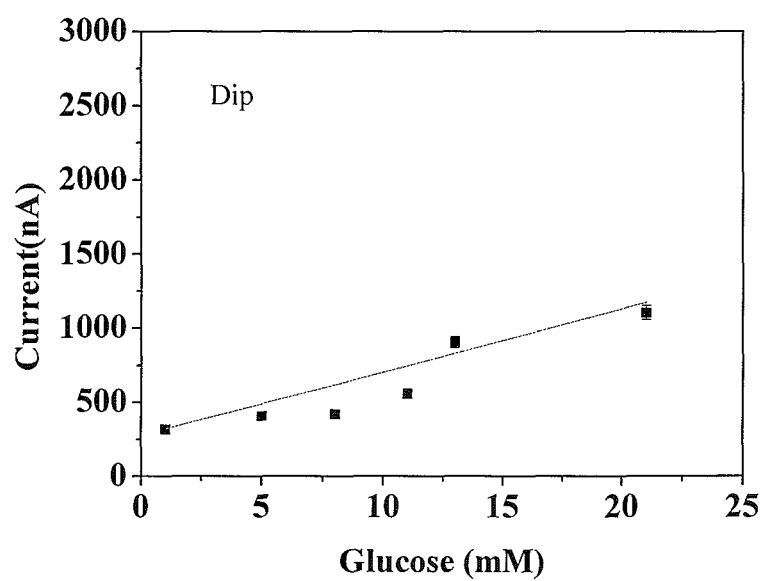
FIG. 15 is a sensitivity testing result of the conventional non-electrospun PVA film.

Generally, the concentration of urea in normal human blood is about 5 mM. Urea is the most common interference substance when using the glucose biosensor. With reference to FIG. 15 and Table 4, a current value (nA)-concentration curve of the present invention is shown. The current values of the present invention are tested with and without addition of urea. The result shows that the current values have no obvious change when adding urea in testing the glucose solution. The present invention is able to avoid the interference substance like urea in the testing blood.

TABLE 4

|  | Current value (nA) |
| --- | --- |
| 5 mM glucose | 450.85 +/− 31.87 |
| 5 mM glucose/urea | 431.72 +/− 61.21 |

The conventional glucose biosensor needs to be preserved in a low temperature environment due to the active GOx inside. Although preserved in a low temperature, the efficiency and sensitivity of the conventional glucose biosensor still reduce after a period of time. With reference to FIG. 16, the present invention still has a high efficiency and sensitivity in the 7$^{th}$ day when preserved at 4 degree Celsius.

The electrospun nanofibrous membrane in accordance with the present invention has at least the following advantages and benefits:

1. The present invention is able to solve the interference problem from $H_2O_2$ during blood testing by using the potassium hexacyanoferrate(III) salt, with the potassium hexacyanoferrate(III) also being low cost.

2. The present invention is able to enhance the sensitivity of the glucose biosensor by adding the conductive material. The best performance of gold nanoparticles, added in PVA/GOx membranes, have a sensitivity of 37.7 μA/mM and a response time of 5.7 sec. Membranes with added graphene showed a higher sensitivity, but a longer response time. The activities of the immobilized enzyme in the PVA/GOx membrane with and without graphene added were 0.93 and 0.56 U/mg, respectively. These results indicate that the presence of graphene contributes to the maintenance of the enzyme's conformational stability which in turn facilitates the catalytic reaction while extending its working lifespan.

3. The present invention may be successfully applied on the disposable glucose biosensor. The glucose biosensor has many advantages like being easy to use, of low cost and having fast reaction time.

What is claimed is:

1. A disposable glucose biosensor comprising:
    a sensor body and an electrode set mounted on the sensor body; and
    an electrospun nanofibrous membrane attached on the electrode set, wherein the electrospun nanofibrous membrane is formed by multiple electrospun nanofibers, wherein each nanofiber is a polyvinyl alcohol (PVA) electrospun nanofiber containing glucose oxidase and potassium hexacyanoferrate(III) homogeneously dispersed therein, wherein the electrospun nanofibrous membrane is cross-linked by glutaraldehyde vapor or heat treatment, wherein the PVA electrospun nanofiber containing glucose oxidase and potassium hexacyanoferrate(III) homogeneously dispersed therein comprises a conductive material, wherein the conductive material is nano-gold attached to the electrospun nanofibrous membrane; and wherein a solid content of the nano-gold in the PVA electrospun nanofiber containing glucose oxidase and potassium hexacyanoferrate(III) homogeneously dispersed therein is in a range of 10~2000 ppm.

2. The disposable glucose biosensor as claimed in claim 1, wherein:
    a solid content of the PVA in the electrospun nanofibrous membrane is in a range of 90%~96%;
    a solid content of the glucose oxidase in the electrospun nanofibrous membrane is in a range of 1~3%; and
    a solid content of the potassium hexacyanoferrate(III) in the electrospun nanofibrous membrane is in a range of 2~8%.

3. An electrospun nanofibrous membrane comprising:
    multiple electrospun nanofibers, wherein:
        the multiple electrospun nanofibers are electrospun by a matrix material solution and containing glucose oxidase and potassium hexacyanoferrate(III) homogeneously dispersed therein; and
        the electrospun nanofibers are cross-linked by glutaraldehyde vapor or heat treatment; and
    a conductive material, wherein:
        the conductive material is nano-gold which is attached to or mounted in the multiple electrospun nanofibers; and
    a solid content of the nano-gold in the multiple electrospun nanofibers is in a range of 10~2000 ppm.

4. The electrospun nanofibrous membrane as claimed in claim 3, wherein the matrix material solution is a polyvinyl alcohol (PVA) solution and the multiple electrospun nanofibers are PVA nanofibers, and wherein the PVA nanofibers are cross-linked by the glutaraldehyde vapor with ultrasonic energy assistance.

5. The electrospun nanofibrous membrane as claimed in claim 4, wherein:
    a solid content of the PVA in the electrospun nanofibrous membrane is 90%~96%;
    a solid content of the glucose oxidase in the electrospun nanofibrous membrane is 1~3%; and
    a solid content of the potassium hexacyanoferrate(III) in the electrospun nanofibrous membrane is 2~8%.

6. The electrospun nanofibrous membrane as claimed in claim 5, wherein the nano-gold is attached to the multiple electrospun nanofibers.

* * * * *